(12) United States Patent
Gunn et al.

(10) Patent No.: US 11,491,050 B2
(45) Date of Patent: Nov. 8, 2022

(54) DEVICES AND METHODS FOR A CANNULA-DELIVERED TREATMENT MATERIAL APPLICATION DEVICE

(71) Applicant: Novartis AG, Basel (CH)

(72) Inventors: Nicholas Max Gunn, Newport Beach, CA (US); Andrew David Johnson, Laguna Niguel, CA (US); Pooria Sharif Kashani, Irvine, CA (US)

(73) Assignee: Alcon Inc., Fribourg (CH)

( * ) Notice: Subject to any disclaimer, the term of this patent is extended or adjusted under 35 U.S.C. 154(b) by 202 days.

(21) Appl. No.: 16/675,576

(22) Filed: Nov. 6, 2019

(65) Prior Publication Data

US 2020/0069465 A1 Mar. 5, 2020

Related U.S. Application Data

(63) Continuation of application No. 15/378,257, filed on Dec. 14, 2016, now Pat. No. 10,500,090.

(60) Provisional application No. 62/268,009, filed on Dec. 16, 2015.

(51) Int. Cl.
*A61F 9/00* (2006.01)
*A61F 9/007* (2006.01)
*A61B 17/34* (2006.01)

(52) U.S. Cl.
CPC ........ *A61F 9/0008* (2013.01); *A61B 17/3421* (2013.01); *A61F 9/007* (2013.01); *A61F 9/00727* (2013.01)

(58) Field of Classification Search
CPC .... A61B 17/3421; A61F 9/0008; A61F 9/007; A61F 9/00727
See application file for complete search history.

(56) References Cited

U.S. PATENT DOCUMENTS

| | | | |
|---|---|---|---|
| 7,524,310 B2 | 4/2009 | Meyer | |
| 7,857,782 B2 | 12/2010 | Tu | |
| 2005/0245881 A1 | 11/2005 | Meyer | |
| 2007/0191863 A1* | 8/2007 | De Juan | A61F 11/00 606/108 |
| 2007/0233037 A1* | 10/2007 | Gifford, III | A61F 9/0008 604/521 |
| 2015/0359529 A1 | 12/2015 | Ganiban | |

FOREIGN PATENT DOCUMENTS

| | | |
|---|---|---|
| CN | 2551263 Y | 5/2003 |
| CN | 103284833 A | 9/2013 |
| WO | 2004087002 A1 | 10/2004 |

* cited by examiner

*Primary Examiner* — Brandy S Lee

(57) ABSTRACT

Methods and systems for performing an ophthalmic surgical treatment procedure include one or more wicking members to secure a volume of treatment fluid to a distal end of a surgical instrument. Such a surgical instrument may include an elongate tubular member having a proximal end, a distal end, and a lumen extending therebetween, the elongate tubular member being configured to penetrate a body cavity of a patient. The instrument may further include a wicking member extending beyond the distal end of the elongate tubular member. The wicking member may be configured to secure a volume of treatment fluid delivered through the lumen to the wicking member for application from the wicking member to target tissue in the body cavity.

17 Claims, 8 Drawing Sheets

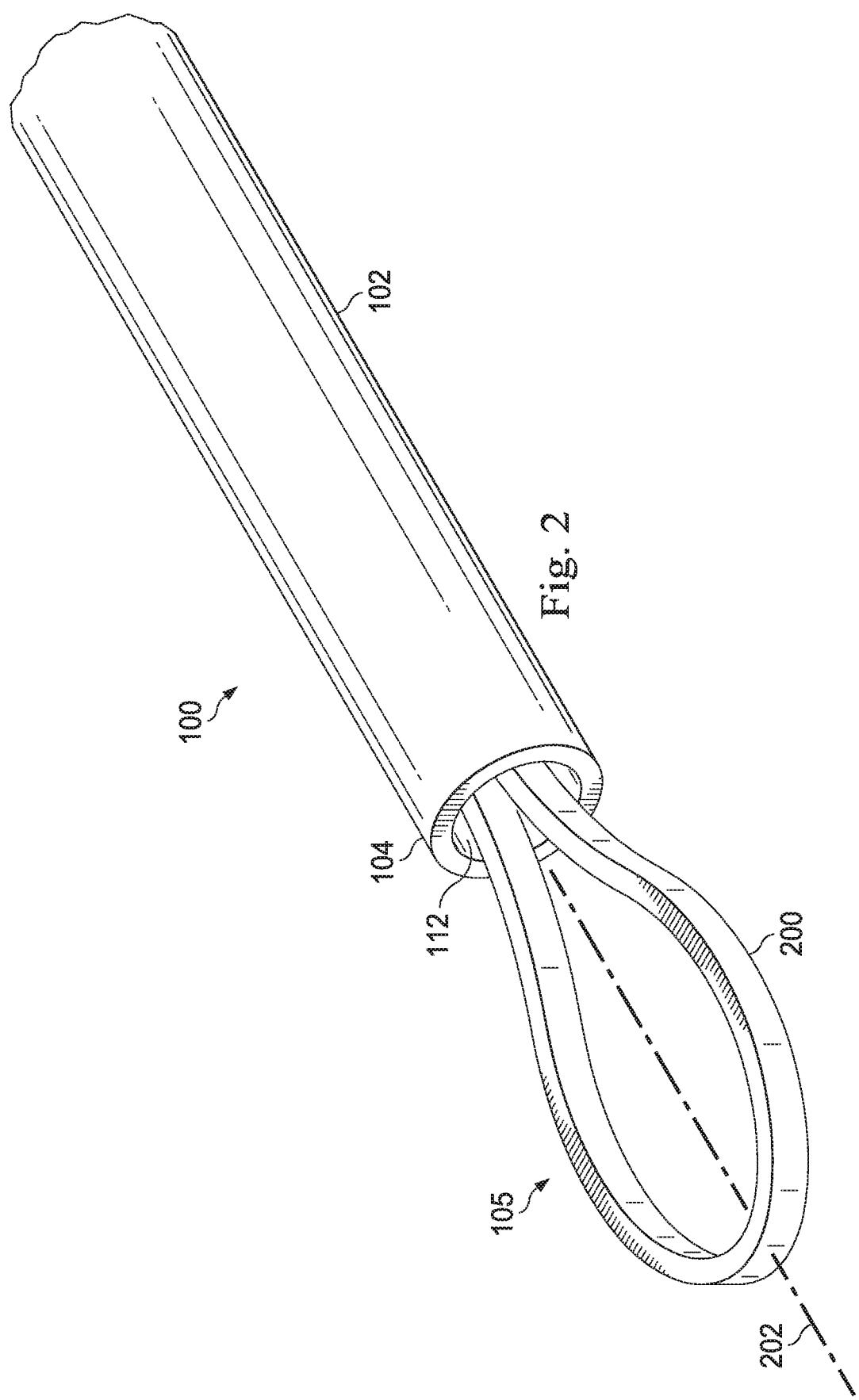

DEVICES AND METHODS FOR A CANNULA-DELIVERED TREATMENT MATERIAL APPLICATION DEVICE

This application:

(a) is a continuation application of U.S. patent application Ser. No. 15/378,257 titled "Devices and Methods for a Cannula-Delivered Treatment Material Application Device" which was filed Dec. 14, 2016 whose inventors are Nicholas Max Gunn, Andrew David Johnson, and Pooria Sharif Kashani which is hereby incorporated by reference in its entirety as though fully and completely set forth herein, and (b) claims the benefit of priority of U.S. Provisional Application Ser. No. 62/268,009 (U.S. patent application Ser. No. 15/378,257 claimed the benefit of priority of provisional application Ser. No. 62/268,009 titled "Devices and Methods for a Cannula-Delivered Treatment Material Application Device" filed on Dec. 16, 2015, whose inventors are Nicholas Max Gunn, Andrew David Johnson, and Pooria Sharif Kashani), which is also hereby incorporated by reference in its entirety as though fully and completely set forth herein.

TECHNICAL FIELD

The present disclosure is directed to methods and systems for applying a treatment material to tissue present within a body cavity, and more particularly to a treatment material application device for use in intraocular procedures.

BACKGROUND

Intraocular procedures are commonly performed to treat many serious conditions of the posterior segment of the eye. For example, vitreo-retinal procedures may treat conditions such as age-related macular degeneration (AMD), diabetic retinopathy and diabetic vitreous hemorrhage, macular hole, epiretinal membrane, cytomegalovirus (CMV) retinitis, retinal detachment/tearing, and many other ophthalmic conditions.

A surgeon may perform intraocular or other intra-cavity procedures with a microscope and special lenses designed to provide a clear image of the interior of the cavity. Access to cavities is provided through several tiny incisions just a millimeter or so in diameter, which are made on the sclera at the pars plana to allow access to the inside of the eye. The surgeon inserts microsurgical instruments through the incisions, such as a fiber optic light source to illuminate inside the eye, an infusion line to maintain the intraocular pressure within the eye and the eye's shape during surgery, and instruments to cut and remove the vitreous body or to perform other surgical operations. A separate incision may be provided for each microsurgical instrument when using multiple instruments simultaneously.

With respect to retinal detachment/tearing, as one treatment option the surgeon may introduce a bubble of gas into the eye of the patient to secure the detached/torn retina against the sclera of the eye. While the gas bubble may dissipate over a period of weeks, proper positioning of the patient's head during that period may be required so that the gas bubble applies pressure in the required direction. While the procedure is simple and cost-effective, the requirement to maintain a specific position in which the head faces down can be onerous. Accordingly, this approach and other approaches to current treatment of tissue tears within a body cavity, such as retinal detachment/tearing within the eye, have not proven entirely satisfactory.

SUMMARY

The systems and methods of the present disclosure are directed to exemplary material application devices for use in intracavity delivery of a treatment fluid. One or more wicking members secure the treatment fluid to an elongate tubular member while it is positioned inside a body cavity.

In some exemplary aspects, the present disclosure is directed to an ophthalmic surgical instrument that may include an elongate tubular member having a proximal end, a distal end, and a lumen extending therebetween, the elongate tubular member may be configured to penetrate a body cavity of a patient. The instrument may further include a wicking member extending beyond the distal end of the elongate tubular member. The wicking member may be configured to secure a volume of treatment fluid delivered through the lumen to the wicking member for application from the wicking member to target tissue in the body cavity.

In some aspects, the ophthalmic surgical instrument may further include a fluid source coupled to the lumen of the elongate tubular member. The wicking member may be a loop of material extending out from the lumen of the elongate tubular member. The loop of material may be retractable into the lumen and extendable therefrom. The material may be an elastomer, a metal, a shape-memory material, a polymer, or a glass. The wicking member may include a plurality of fibers extending from the distal end of the elongate tubular member, in some implementations. The treatment fluid may be a tissue adhesive.

The present disclosure also discloses a surgical instrument that may include an elongate tubular member, a fluid source, and a wicking member. The elongate tubular member may have a proximal end, a distal end, and a lumen extending therebetween, and being configured and sized for insertion into a cavity of a patient. The fluid source may be coupled to the lumen of the elongate tubular member. The wicking member may extend beyond the distal end of the elongate tubular member. The wicking member may be configured to wick secure a volume of treatment fluid delivered through the lumen to the wicking member for application from the wicking member to target tissue in the cavity.

In some aspects, the wicking member of the surgical instrument may be deployable from the distal end of the elongate tubular member. The wicking member may have a substantially rectangular cross section. The fluid source may be configured to dispense fluid through the lumen as the wicking member is deployed beyond the distal end of the elongate tubular member. The wicking member may include a plurality of fibers fixed to the distal end of the elongate tubular member. The fibers may have a hydrophilic coating or be made from a hydrophilic material. The fibers may be made from polymer, metal, shape-memory material, glass, silicone, silicone rubber, or other elastomer. In some implementations, the distal end of the elongate tubular member may be capped and may include a plurality of openings formed therein to permit the fluid to pass from the lumen to the fibers. The diameter of the lumen or the elongate tubular member may be in a range from about 0.2 mm (millimeters) to about 0.6 mm.

The present disclosure also discloses methods of using such a surgical instrument. The method may include operations or steps of deploying a wicking member from a distal end of the surgical instrument, dispensing a volume of a treatment fluid from a lumen extending at least partially through the surgical instrument at the distal end of the surgical instrument, the volume of the treatment fluid being bound to the wicking member by microfluidic forces, and transferring the volume of the treatment fluid to a portion of tissue at a surgical treatment site.

In some implementations, the methods may further include partially curing the volume of the treatment fluid prior to transferring the volume of the treatment fluid to the portion of tissue at the surgical treatment site. The portion of tissue at the surgical treatment site may be a portion of retinal tissue within an eye of a patient. The volume of the treatment fluid may form a treatment film. In some implementations, deploying the wicking member from the distal end of the surgical instrument and dispensing the volume of the treatment fluid from the lumen may be performed simultaneously.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the accompanying drawings and the following detailed description.

BRIEF DESCRIPTION OF THE DRAWINGS

The accompanying drawings illustrate implementations of the instruments, devices, and methods disclosed herein and together with the description, serve to explain the principles of the present disclosure.

FIG. 2 is a perspective view of a distal end of the exemplary surgical instrument of FIG. 1, according to aspects of the present disclosure.

Figure 1:
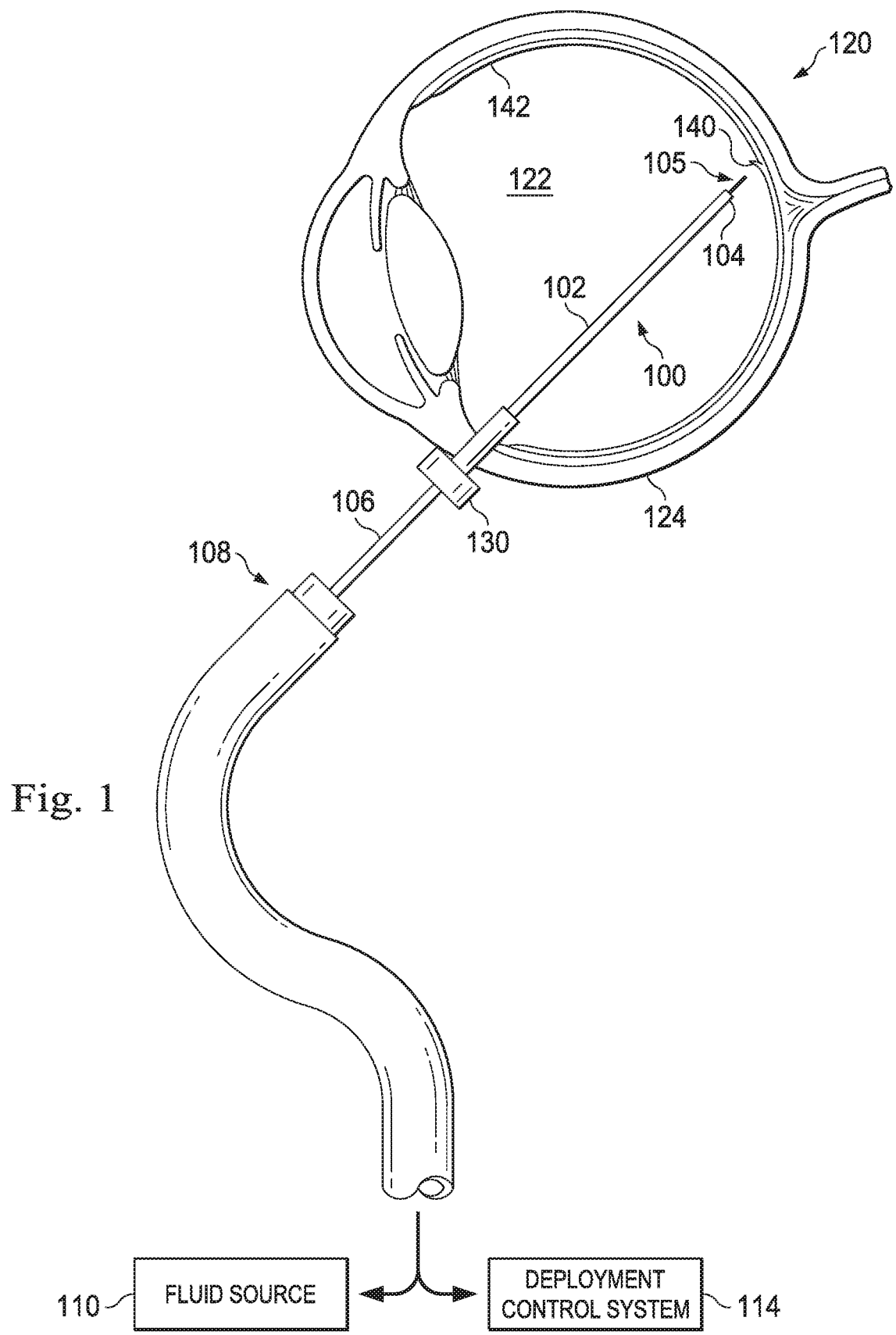
FIG. 1 is an illustration of an exemplary surgical instrument for material application in an eye, according to aspects of the present disclosure.

The accompanying drawings may be better understood by reference to the following detailed description.

DETAILED DESCRIPTION

For the purposes of promoting an understanding of the principles of the present disclosure, reference will now be made to the implementations illustrated in the drawings, and specific language will be used to describe the same. It will nevertheless be understood that no limitation of the scope of the disclosure is intended. For example, some more specific implementations of the present disclosure are directed to surgical instruments usable in ophthalmic surgical treatments to apply a material to a treatment site within the eye; however, the application of the principles of the present disclosure to material application devices usable in other surgical procedures is within the scope of this disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure. For simplicity, in some instances the same reference numbers are used throughout the drawings to refer to the same or like parts.

The present disclosure is directed to surgical instruments or devices that provide for the application of a material to a tissue treatment site to secure the tissue at the site in position. One or more surgical instruments may be inserted through a cannula device, such as a trocar, in order to perform a surgical treatment within a cavity. The surgical instrument may be a treatment material application device that can deliver a treatment material in a fluid state to target tissue within a body cavity during the treatment performed therein. In some examples, the body cavity is the vitreous chamber of an eye.

FIG. 1 illustrates a use of a surgical instrument 100 in an ophthalmic procedure. The surgical instrument 100 may be referred to as a material application device. The surgical instrument 100 may include an elongate tubular member 102 having a distal end 104 and a proximal end 106. As is discussed in greater detail herein, the distal end 104 includes components that allow for the application of a treatment material or treatment fluid, such as a tissue adhesive, to a target portion of a treatment site within the eye 120 (as shown in the illustrated example) or another body cavity.

As illustrated, the elongate tubular member 102 of the surgical instrument 100 accesses a vitreous chamber 122 of the eye 120 through an incision formed through the sclera 124 of the eye 120. As shown in FIG. 1, a cannula device 130, such as a trocar, providing access through the incision in the sclera 124 to the vitreous chamber 122. The cannula device 130 includes a lumen formed therethrough through which the elongate tubular member 102 of the surgical instrument 100 may pass to gain access to the vitreous chamber 122.

The proximal end 106 of the elongate tubular member 102 may couple to a distal end of a tubing 108. In some embodiments, the tubing 108 is flexible; while in other embodiments, the tubing 108 may be rigid. FIG. 1 illustrates an embodiment with flexible tubing 108. The flexible tubing 108 may include one or more lumens to conduct a treatment material from a fluid source system 110. The fluid source system 110 may include a reservoir and a dispensing system, such as a plunger or pressure source that, when activated, causes a fluid from the reservoir to be dispensed or injected through a lumen 112 (shown in FIG. 2) of the elongate tubular member 102. The flexible tubing 108 may provide access between the proximal end 106 of the surgical instrument 100 and a deployment control system 114. The deployment control system 114 is configured to deploy a wicking member or material applicator 105 from the distal end 104 of the elongate tubular member 102, as is discussed in greater detail herein. The wicking member or material applicator 105 may secure the fluid in place while the elongate tubular member 102 is manipulated to position the volume of fluid proximate a treatment site. The deployment control system 114 may physically contact or connect with the material applicator 105 to extend the material applicator 105 from the distal end 104 and to retract the material applicator 105 back into the lumen 112 of the elongate tubular member. The deployment control system 114 may include motors, sliders, gears, plungers, and/or other actuators or mechanisms.

In some implementations of the surgical instrument 100, the fluid source system 110 and the deployment control system 114 may be jointly operable such that a single control, such as a slider, may be used by a surgeon or other user to direct both the deployment of the material applicator 105 from the distal end 104 and the dispensing or injection of a treatment fluid into the vitreous chamber 122. The deployment and the injection may be performed in proportion to or in relation to each other, such that the volume of treatment fluid injected into the vitreous chamber corresponds to a length of the material applicator 105 extending beyond the distal end 104 or a volume defined thereby. In other implementations of the surgical instrument 100, the fluid source system 110 and the deployment control system 114 may be operated separately by separate controls, such as by control of a console or other controller.

A surgeon may operate the surgical instrument 100 to deploy the material applicator 105 from the distal end 104 of the elongate tubular member 102 and to dispense a volume of treatment fluid through the lumen 112 to the material applicator 105. Microfluidic forces, such as surface tension and/or capillary forces, may cause the volume of fluid (e.g., a drop of fluid) to temporarily adhere to the material applicator 105. The surgeon may manipulate the surgical instrument 100 to position the material applicator 105 near the treatment site 140, which may be a portion of the retina 142 of the eye 120. In some implementations, the treatment fluid is a tissue adhesive that, when cured, seals a hole or break in the retina 142 or secures a detached or torn portion of the retina 142 in position to permit a natural healing process to occur to repair the retina. For example, the treatment fluid may be a liquid bandage that provides a barrier to fluid ingress through a hole or break in the retina to prevent fluid accumulation in the sub-retinal space. The treatment fluid may also provide structural support to keep the detached or torn portion of the retina 142 in position. In some embodiments, the treatment fluid may also include a biologically active agent such as a drug. The treatment fluid may be used to retain the drug at the desired position for the period of treatment.

FIG. 2 is a perspective view of the surgical instrument 100, according to some implementations of the present disclosure. FIG. 2 illustrates a portion of the elongate tubular member 102 and provides additional detail regarding the distal end 104 thereof. As can be seen in FIG. 2, the material applicator 105 is shown protruding from or beyond the distal end 104 and through the lumen 112, which extends at least partially through the elongate tubular member 102. This couples to the fluid source system 110 of FIG. 1. In the example in FIG. 2, the material applicator 105 includes a ribbon 200. Both ends of the ribbon 200 may remain within the lumen 112 during utilization of the surgical instrument 100, such that the ribbon 200 forms a loop that protrudes from the distal end 104. The ribbon 200 may have a substantially rectangular cross-section and may be formed from any suitable material. Examples of suitable materials include a polymer, glass, nitinol, or another metal material. The ribbon 200 may be more rigid with respect to a major axis of the rectangular cross-section thereof than with respect to the minor axis of the rectangular cross-section thereof. The ribbon 200 may be configured to flex to fit within the lumen 112. In some instances, it elastically moves from a retracted, collapsed position in the lumen 112, to a deployed, expanded condition as shown in FIG. 2. Here, the ribbon 200 is expanded to have a loop width greater than a diameter of the lumen 112. Some implementations of the ribbon 200 may have an oval or other shaped cross-section. The surface of the ribbon 200 may be hydrophilic due to the material from which it is formed or due to a surface treatment.

Additionally, some implementations of the material applicator 105 may include more than one ribbon 200. For example, a particular implementation may include two or more ribbons 200. The ribbons 200 may be independently deployed from the distal end 104, which may enable a user to shape a volume of fluid dispensed from the lumen 112 or may enable the material applicator 105 to hold a greater volume of fluid for application at a treatment site.

The ribbon 200 may be moved by the deployment control system 114 along the axis 202 (not explicitly illustrated in FIG. 2), which may be a central axis of the elongate tubular member 102. Accordingly, the deployment control system 114 may be activated to deploy the ribbon 200 from the lumen 112 and may be activated to retract the ribbon 200 back into the lumen 112. The lumen 112 may range from about 0.2 mm to about 0.6 mm, according to various implementations. In some implementations, the elongate tubular member 102 may be a needle having a gauge size ranging from about 20 gauge to about 27 gauge. Other sizes, larger and smaller are contemplated.

Figure 3A:
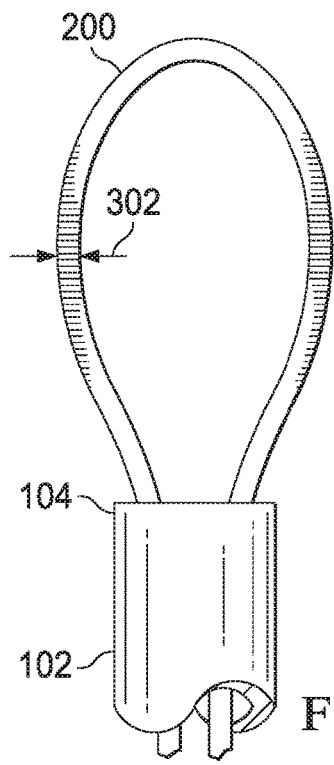
FIGS. 3A and 3B illustrate a top view and a side view, respectively, of the exemplary surgical instrument of FIG. 2, according to aspects of the present disclosure.
Figure 3B:
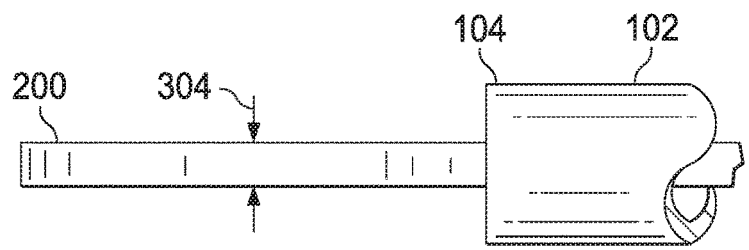

FIGS. 3A and 3B are a top view and a side view of the surgical instrument 100 in a deployed state as shown in FIG. 2. The top view of FIG. 3A illustrates the minor axis or thickness 302 of the ribbon 200. The side view of FIG. 3B illustrates the major axis or width 304 of the ribbon 200. The thickness 302 of the ribbon 200 may range from about 0.01 mm to about 0.1 mm. The width 304 of the ribbon 200 may range from about 0.05 mm to about 0.5 mm. Other thicknesses and widths, larger and smaller are contemplated.

Figure 4A:
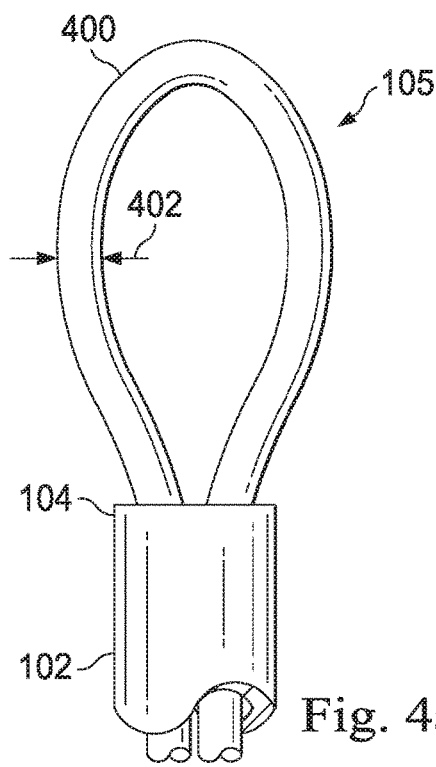
FIGS. 4A and 4B illustrate a top view and a side view, respectively, of an alternative implementation of the exemplary surgical instrument of FIG. 1, according to aspects of the present disclosure.
Figure 4B:
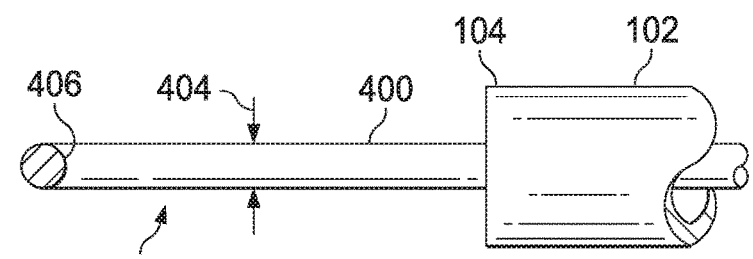

Referring now to FIGS. 4A and 4B, shown therein are a top view and a side view of an alternative implementation of the surgical instrument 100, in which the material applicator 105 is not provided by the ribbon 200. Instead, the material applicator 105 includes a fiber 400. The thickness 402 of the fiber 400 may be equal to the width 404 of the fiber 400. In some implementations of the fiber 400, the fiber 400 has a circular cross-section 406. In other implementations of the fiber 400, the cross-section 406 may be square or have another shape. Additionally, some implementations of the material applicator 105 may include more than one fiber 400, and other implementations may include fibers that are not looped but that can be deployed from the distal end 104 out of the lumen 112. These implementations may provide opportunities to shape the volume of treatment material to be delivered to a desired tissue treatment site.

Figure 5C:
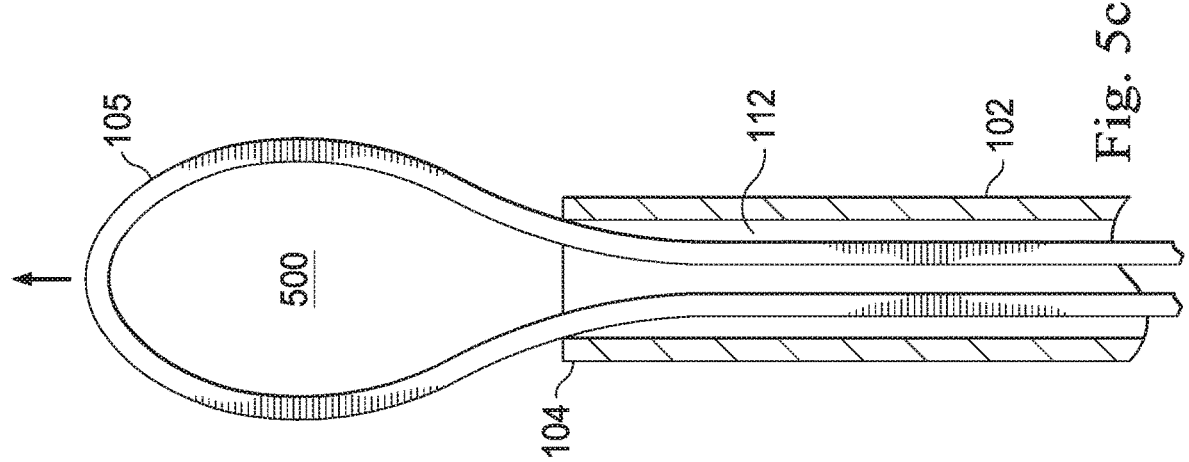
FIGS. 5A, 5B, and 5C illustrate an exemplary surgical instrument during a deployment process, according to aspects of the present disclosure.
Figure 5B:
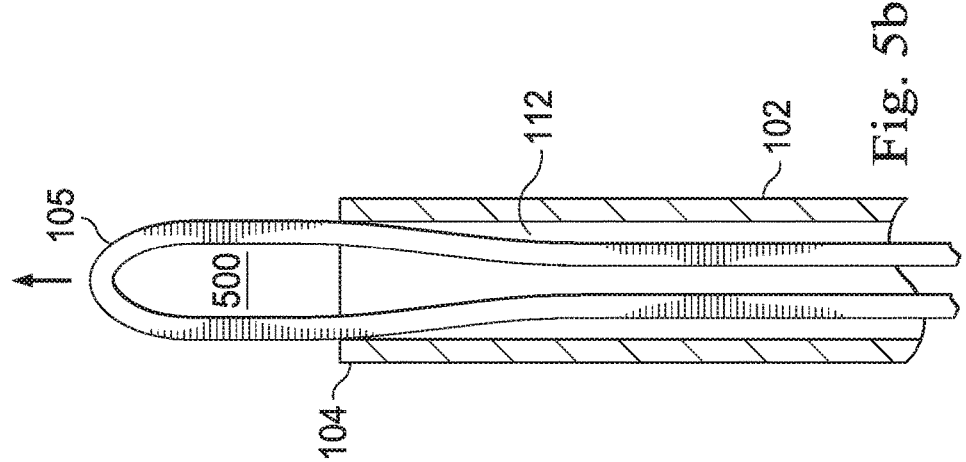
Figure 5A:
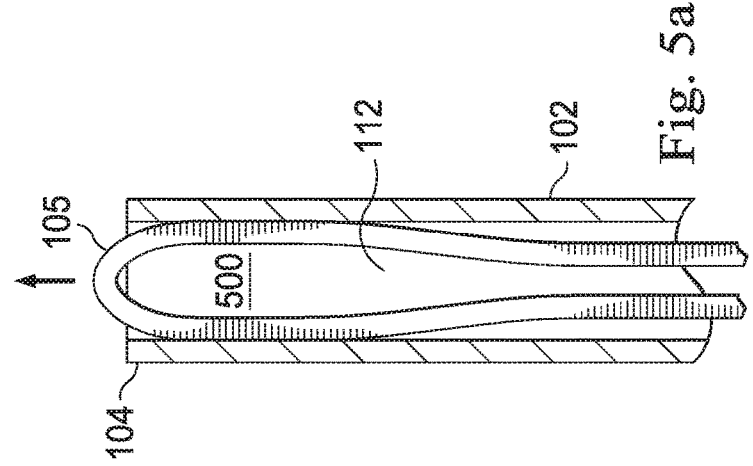

Referring now to FIGS. 5A, 5B, and 5C, shown therein is a cross-section of the surgical instrument 100 of FIG. 1 in three different states of deployment. FIG. 5A shows the material applicator 105 fully contained within the lumen 112 of the elongate tubular member 102. The walls of the lumen 112 compress the width of the loop 500. As shown in the cross-section of FIG. 5A, the material applicator 105 forms a loop 500. As the material applicator 105 is partially deployed from the lumen 112 at the distal end 104, a portion of the loop 500 is exposed as shown in FIG. 5B. FIG. 5C shows the loop 500 of the material applicator 105 in a fully deployed state. In the fully deployed state, the flexible nature of the loop 500 allows the loop 500 to have a width greater than the diameter of the lumen 112. The material applicator 105 may be deployed by the deployment control system 114. In some implementations, the ends of the material applicator 105 (e.g., the ends of the ribbon 200 or the fiber 400) may be joined to a carriage plate or other structure that is connected to a plunger or motor of the deployment control system 114. The plate or other supporting structure may be pushed within the lumen 112 to deploy the material applicator 105 therefrom, forming the expanded loop 500 shown in FIG. 5C. The material applicator 105 may be deployed beyond the distal end 104 of the elongate tubular member 102 and may be retracted or pulled back into the lumen 112 by the deployment control system 114.

Figure 6A:
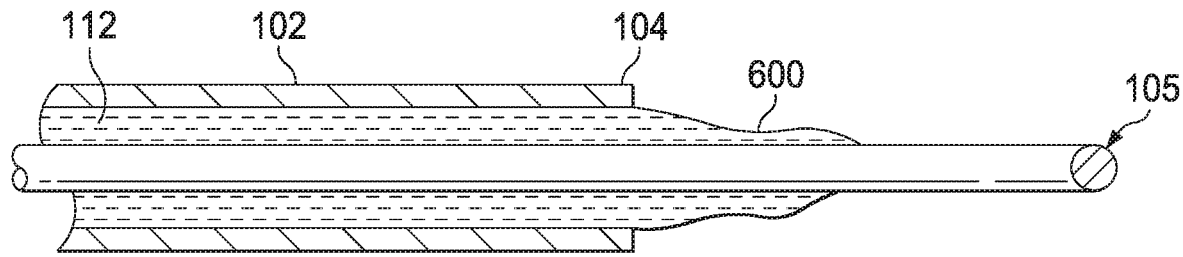
FIGS. 6A, 6B, and 6C illustrate an exemplary surgical instrument during a treatment material dispensing process, according to aspects of the present disclosure.
Figure 6B:
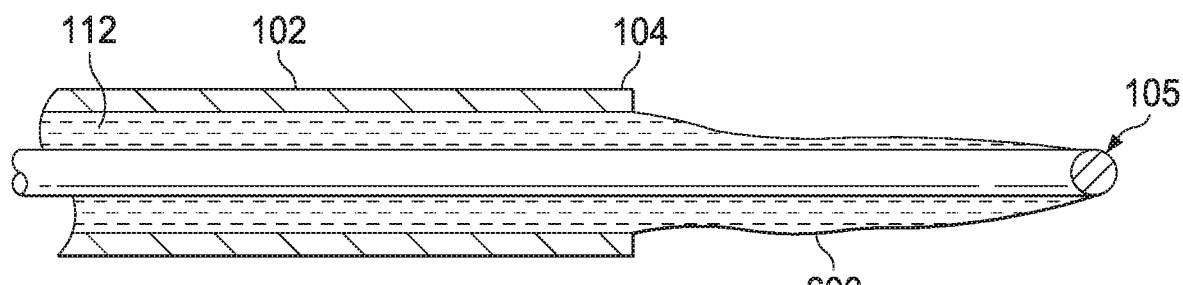
Figure 6C:
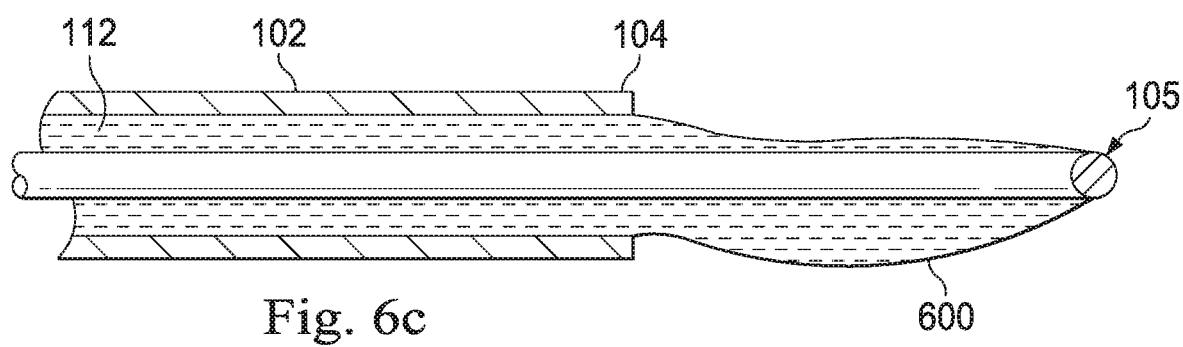

Referring now to FIGS. 6A, 6B, and 6C, shown therein is an implementation of the surgical instrument 100 of FIG. 1 having different volumes of fluid held by the material applicator 105. The fluid source system 110 may be activated to cause fluid 600 to travel from a reservoir of the fluid source system 110 through the flexible tubing 108 and through the lumen 112 of the elongate tubular member 102. Because of the scale of the surgical instrument 100, and particularly of the elongate tubular member 102, the fluid 600 may be subjected to microfluidic forces, such that surface interactions and viscosity dominate over gravitational forces given the scale of the surgical instrument 100.

As shown in FIG. 6A-C, when the fluid 600 reaches the distal end 104 of the elongate tubular member 102, the material applicator 105 wicks the fluid 600 into the loop 500 as shown in FIG. 5C. The wicking action may be driven by the interaction between the fluid 600 and the hydrophilic surface of loop 500. When the fluid 600 first fills the area defined by the loop 500, the thickness of the film formed by the fluid 600 may be less than a thickness or width of the material applicator 105. As additional fluid 600 is dispensed out of the lumen 112, the amount of fluid 600 within the loop 500 increases as seen in FIGS. 6B and 6C. In operation, after a film of the fluid 600 is formed within loop 500 of the material applicator 105, the surgeon may wait for a period of time before placing the film in contact with the tissue treatment site. The period of time may allow the fluid 600 to partially cure in air or by subjection to actinic energy, such as ultraviolet or visible light radiation. In some embodiments, the fluid may be a two-part combination that cures during a period of time after the two parts are mixed, which may occur as the fluid 600 (including the two parts) passes through the elongate tubular member 102 or before introduction into the elongate tubular member 102. The period of time may range from a few second to several minutes, during which the fluid may be positioned. The fluid 600 may take a gel-like viscosity in the partially cured state. This may enable it to stay on the material applicator 105 until it is positioned to secure tissue in place, avoiding unwanted flowing or dripping of the material. Additionally, the partially cured film of fluid 600 may increase in adhesion and in structural integrity such that it may better secure a portion of detached or torn retina in place. In some implementations, the fluid 600 may decrease in adhesion during the curing process. Accordingly, the surgeon may make contact with the tissue treatment site before the film of fluid 600 is fully cured or even before the film of fluid 600 is partially cured. Accordingly, the fluid 600 may be fully cured after it has been placed in contact with the tissue at the tissue treatment site.

Figure 7:
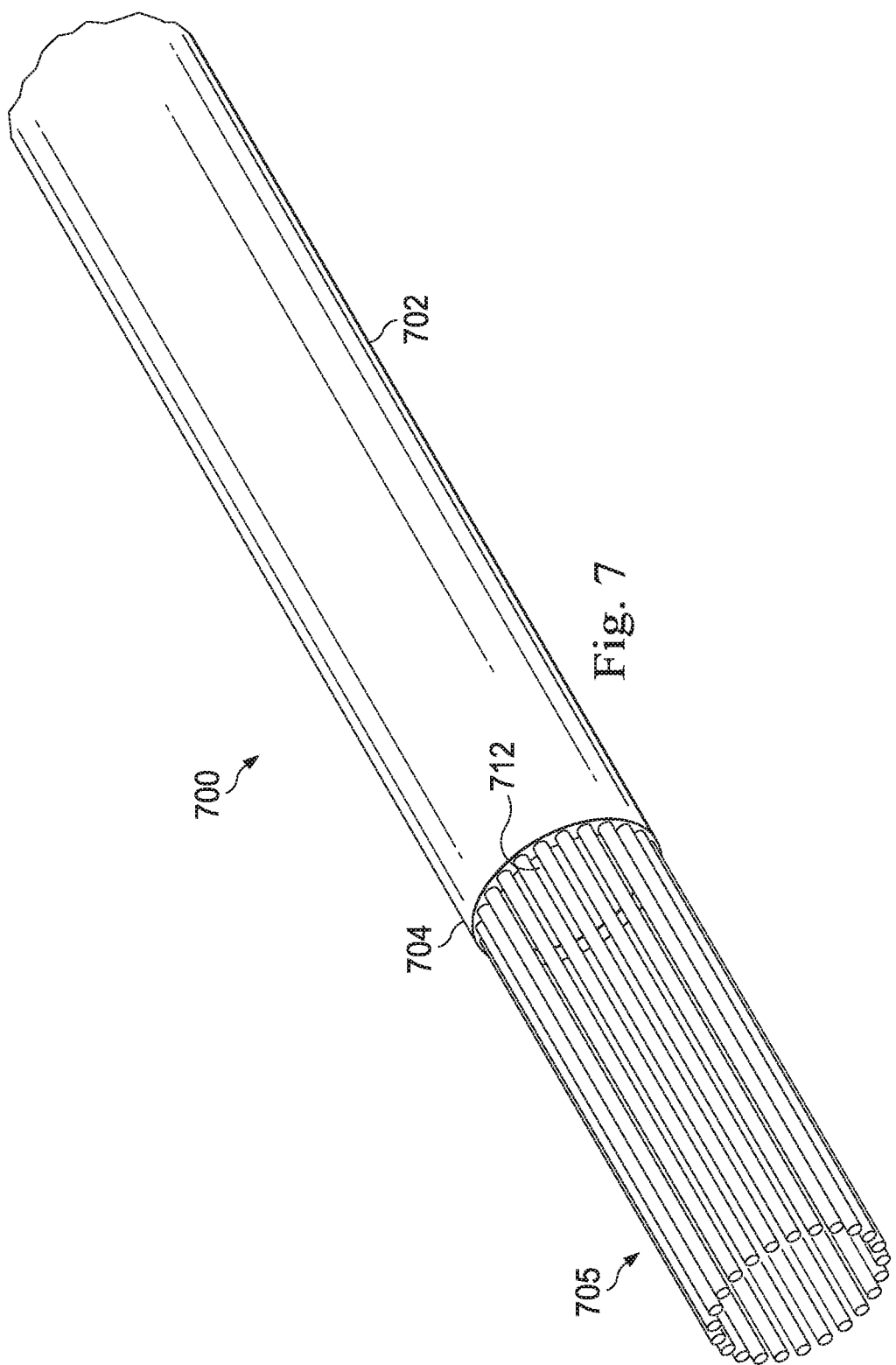
FIG. 7 is a perspective view of an additional exemplary surgical instrument, according to aspects of the present disclosure.

Referring now to FIG. 7, shown therein is an exemplary surgical instrument 700 that may be used to apply a treatment material to tissue at a tissue treatment site within a body cavity, like the vitreous chamber 122 of the eye 120 of FIG. 1. The surgical instrument 700 may include an elongate tubular member 702 having a proximal end, a distal end 704 and a lumen 712 extending therein. The lumen 712 may conduct or convey a fluidic treatment material through the tubular member 702 to a plurality of fibers, collectively referred to as fibers 705. In some implementations, the fibers 705 may be generally-cylindrical members protruding from the distal end 704. The fibers 705 may be made from a flexible material that is hydrophilic or is coated with a hydrophilic material. The fibers 705 may be made from a polymer, glass, or a metal material. When the fluid, such as the fluid 600 described herein, is injected into the body cavity through the lumen 712, the fluid is wicked or drawn forward by the fibers 705. Due to microfluidic forces, the fibers 705 may contain a volume of fluid that can be placed, brushed, or "painted" on tissue at a tissue treatment site.

Figure 8A:
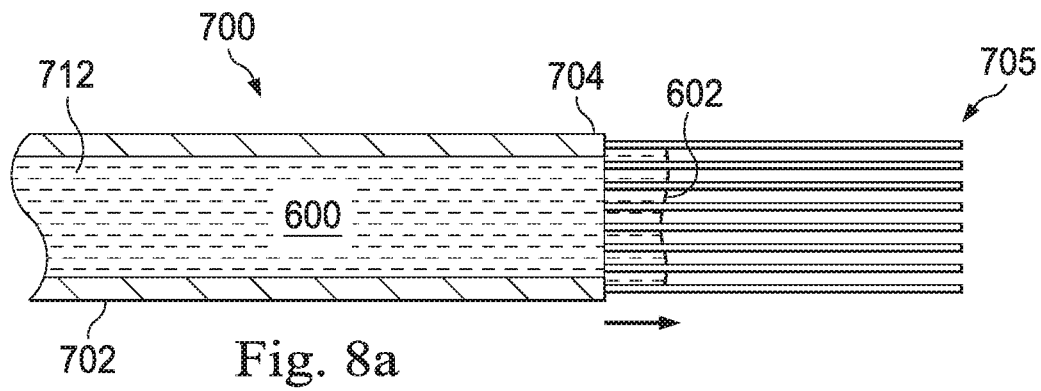
FIGS. 8A, 8B, and 8C are cross-sectional views of the additional exemplary surgical instrument of FIG. 7 during a material dispensing process, according to aspects of the present disclosure.
Figure 8B:
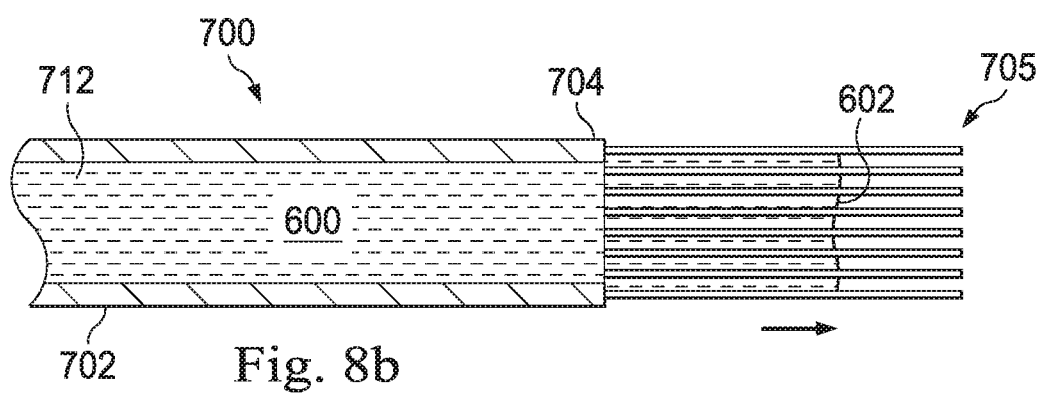
Figure 8C:
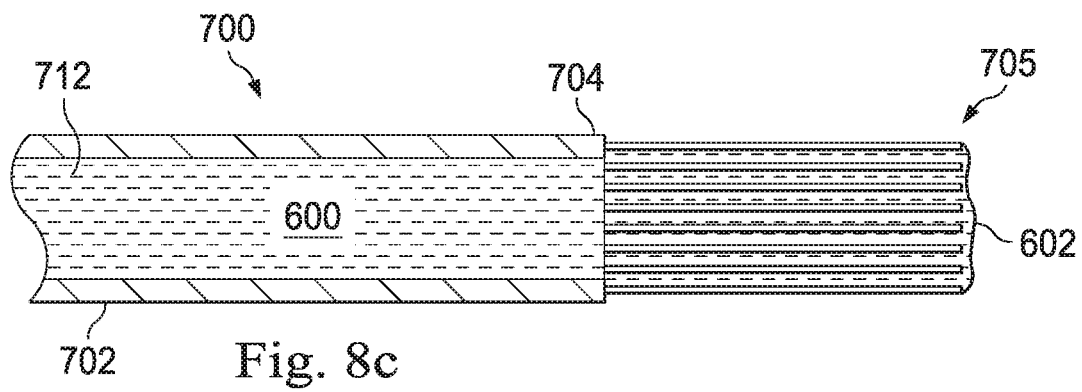

Referring now to FIGS. 8A, 8B, and 8C, shown therein is an implementation of the surgical instrument 700 in various states of a fluid dispensing process. As shown in FIGS. 8A-C, the fluid 600 may be forced through the lumen 712 by the fluid source system 110 of FIG. 1. Some implementations of the surgical instrument 700 include fixed fibers 705 that are fixed in place on a distal surface of the distal end 704. For example, the fibers 705 may be glued, welded, or press fit into corresponding holes to secure the fibers 705 to the distal end 704. In other implementations, the fibers 705 are coupled to a support structure situated within the lumen 712 and can be deployed from the distal end 704 by the deployment control system 114 of FIG. 1.

As shown in FIG. 8A, the proximal ends of the fibers 705 have begun to wick the fluid 600 toward the distal ends of the fibers 705. The separation distance between the fibers 705 may facilitate the microfluidic wicking, such as by capillary forces. As additional fluid 600 is forced through the lumen 712, the front 602 of the fluid 600 progresses toward the distal end of the fibers 705. As shown in FIG. 8C, the front 602 of the fluid 600 progresses beyond the distal ends of the fibers 705 as additional fluid 600 is forced through the lumen 712. As illustrated in FIG. 8C, the fibers 705 may be considered to be "full" of the fluid 600, as a paintbrush can be "filled" with paint. The surgical instrument 700 may be manipulated by the surgeon to brush or "paint" the tissue treatment site with the fluid 600 so that the fluid 600 adheres to the tissue. While the fibers 705 may be hydrophilic, the surface of human tissue within body cavities, such as retinal tissue within the eye, is generally hydrophilic. Accordingly, when the fibers 705 are filled with the fluid 600 and are brought into contact with the tissue treatment site, the fluid 600 is more attracted to the tissue surface then to the fibers 705, causing the fluid 600 to be attracted more to the tissue surface. Additionally, prior to applying the fluid 600 to a tissue treatment site with the fibers 705, the surgeon may wait a period of time to partially cure the fluid 600. Partially curing the fluid 600 may increase the adhesiveness of the surface of the fluid 600, increasing the attraction to the tissue surface.

Figure 9:
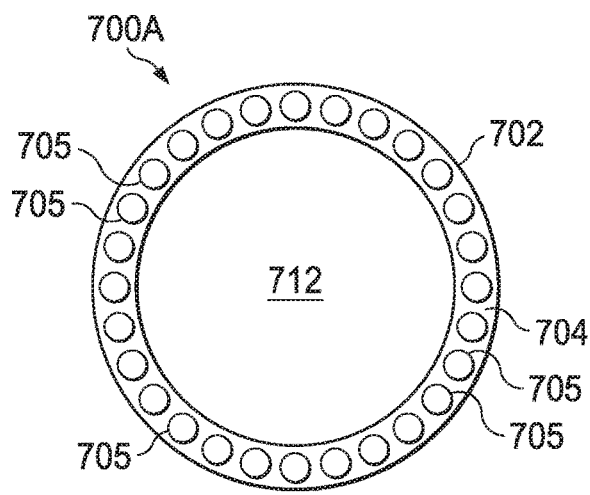
FIG. 9 illustrates an end view of an implementation of the additional exemplary surgical instrument of FIG. 7, according to aspects of the present disclosure.
Figure 10:
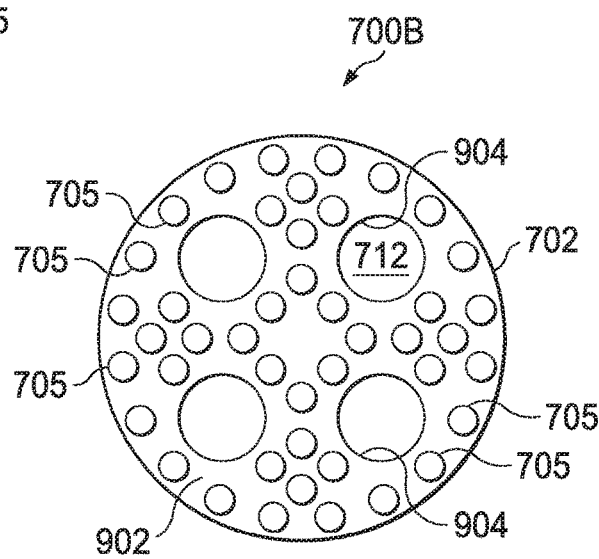
FIG. 10 is an end view of another implementation of the additional exemplary surgical instrument of FIG. 7, according to aspects of the present disclosure.

Referring now to FIG. 9 and FIG. 10, shown therein are alternative end views of the surgical instrument 700A and surgical instrument 700B, which may be implementations of the surgical instrument 700 of FIGS. 7 and 8A-C. As shown in FIG. 9, the distal end 704 of the elongate tubular member 702 of an exemplary surgical instrument 700A has a generally-annular shape. The elongate tubular member 702 of surgical instrument 700A includes the central lumen 712 through which fluid 600 may be delivered to the distal end 704 and to the fibers 705 protruding therefrom. As shown in FIG. 9, the fibers 705 of surgical instrument 700A are arranged in a generally circular configuration corresponding to the annular surface of the distal end 704. The implementation of the surgical instrument 700A shown in FIG. 9 includes around 30 fibers 705. FIG. 10 illustrates in implementation of the surgical instrument 700B that includes an end cap 902. The end cap 902 includes the plurality of fibers 705 protruding therefrom and may also include a plurality of openings 904 that provide access to the lumen 712. In some implementations, each of the plurality of openings 904 corresponds to a separate lumen extending within the elongate tubular member 702. In some implementations, different fluid materials may be provided through different openings 904 and combined by mixture within the region defined by the fibers 705. While the fibers 705 are illustrated as having circular cross-sections, the fibers 705 in other implementations may have different cross-sectional shapes. For example, the fibers 705 may have oval, square, rectangular, octagonal, or other shaped cross-sections. The fibers 705 may be formed from a flexible material such as a polymer, a glass, a metal, or a shape-memory material. Shape-memory materials may include metal alloys, such as Nitinol, as well as non-metal materials, and have the ability to return to an original shape after deformation. Additionally, some implementations of the surgical instrument 700 may include fibers 705 with individual fibers having different cross-sections, different lengths, different diameters, or other differences.

In various implementations of the surgical instrument 700 (including the implementations of 700A and 700B) shown in FIGS. 7, 8A-C, 9 and 10, individual fibers ranging from about 5 µm (micrometers) to about 500 µm in diameter. Some implementations may include fibers ranging from about 50 µm to about 100 µm in diameter. While the implementation in FIG. 9 includes about 30 fibers and the implementation illustrated in FIG. 10 includes about 40 fibers, various implementations may include anywhere from 15 to 100 fibers, although some implementations may include fewer or more fibers. The fibers 705 may range in length from about 0.5 mm to about 1 mm in some implementations, and from about 5 mm to about 10 mm in other implementations. Thus, the fibers 705 may range from about 0.5 mm to about 10 mm in various implementations. Longer and shorter implementations are also contemplated.

Figure 11:
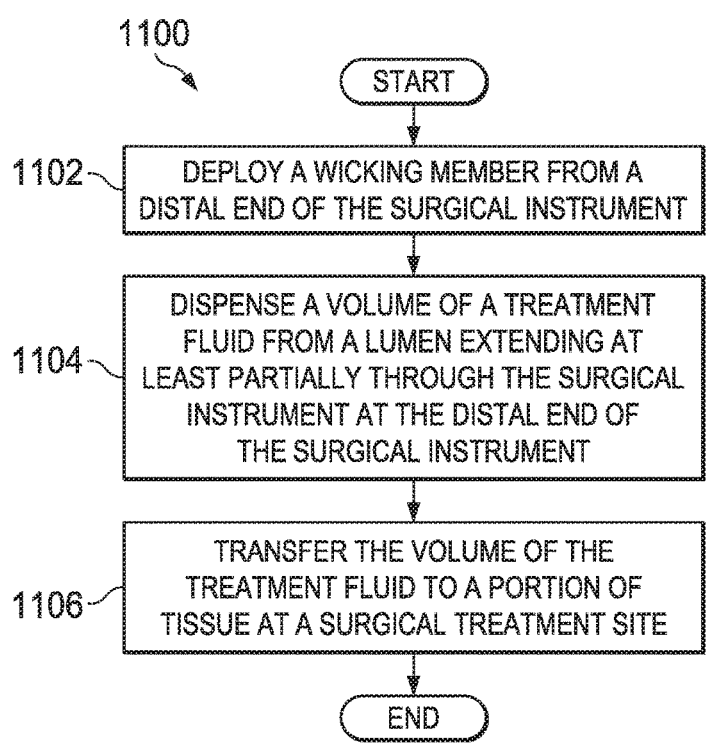
FIG. 11 is a method of applying a treatment material to tissue inside a body cavity, according to aspects of the present disclosure.

Referring now to FIG. 11, shown therein is a flowchart of a method 1100 of using a surgical instrument, according to various implementations of the present disclosure. The method 1100 is illustrated as a series of steps or operations performed in a sequence to bring about a desired conditional result. Implementations of the method 1100 may include additional operations before, after, in between, or as part of the enumerated operations. Additionally, some implementations of the method 1100 may not include all of the enumerated operations.

The method 1100 may begin at 1102, at which a wicking member is deployed from a distal end of the surgical instrument. For example, the wicking member may be a material applicator 105 such as the fibers 705 of FIG. 7, the ribbon 200 of FIG. 2, or the fiber 400 of FIGS. 4A and 4B. In some implementations, the wicking member may have a hydrophilic surface to attract and retain a treatment fluid or treatment material, such as a tissue adhesive that is suited for securing a portion of tissue in a desired position. Exemplary tissue adhesive may include hydrogel-based adhesives, such as poly(ethylene glycol) or PEG-based hydrogels that use anime-reactive chemistry to crosslink into a hydrogel. Other exemplary tissue adhesives may include non-hydrogel adhesives, such as cyanoacrylate.

At 1104, a volume of a treatment fluid may be dispensed from a lumen extending at least partially through the surgical instrument at the distal end of the surgical instrument, the volume of the treatment fluid being bound to the wicking member by microfluidic forces. For example, the fluid source system 110 may be activated by a surgeon to force the treatment fluid through the lumen 112 of the elongate tubular member 102 or the lumen 712 of the elongate tubular member 702 of FIGS. 1 and 7, respectively. As the treatment fluid is forced through the lumen of the surgical instrument, the wicking member or wicking members may draw the treatment fluid distally and secure the treatment fluid to the elongate tubular member to the wicking member, thereby preventing drips, while the surgeon positions the surgical instrument. A volume of the treatment fluid may form within a loop 500 of the material applicator 105 (of surgical instrument 100) or within a volume defined by fibers 705 (of surgical instrument 700). In some implementations, the wicking member may have a higher hydrophilicity, such that the wicking members pull treatment fluid out of the lumen 112 without a pressure or force being applied by the fluid source system 110.

In some implementations, the surgeon may wait for a period of time after the volume of treatment fluid has been dispensed from the distal end of the surgical instrument. The period of time may provide the treatment fluid time to partially cure, which may increase the viscosity of the fluid and may increase the adhesiveness of the surface of the volume of treatment fluid. This may further prevent the volume of treatment fluid from dripping from or otherwise moving from the tissue treatment site due to the influence of gravity, to motions of the surgical site, or to other reasons. In implementations in which the volume of treatment fluid is positioned within a loop, such as the loop 500 as shown in FIGS. 5A-C, the period of time may partially cure the treatment fluid and cause the treatment fluid to form a film that can be applied to treat a portion of tissue. The thickness of the film corresponds to the volume of treatment fluid dispensed from the distal end of the surgical instrument.

At 1106, the volume of the treatment fluid is transferred to the portion of tissue at the surgical treatment site. For example, the surgeon may move the distal end 104 of the surgical instrument 100 to cause the material applicator 105 to contact the tissue at the treatment site 140 of FIG. 1. The adhesiveness of the treatment fluid may be greater with respect to the tissue than to the material applicator 105, such that when the material applicator 105 is retracted, the treatment fluid remains in position at the treatment site. Accordingly, the wicking member may be more hydrophilic than the interior surface of the lumen 112 of the surgical instrument 100 and less hydrophilic than the tissue to be treated. In some implementations, the method 1100 includes a step or operation of partially curing the treatment fluid, which may be done by exposure to air or exposure to actinic energy, such as ultraviolet light or visible light. In implementations in which the treatment fluid is a two-part combination that cures due to the interactions of the two parts, the curing may be provided by waiting a period of time after the components are mixed. More than two components may be included in some implementations. Additionally, after the treatment fluid is positioned into contact with the tissue, the method 1100 may include a curing operation. In some implementations, the curing operation or process may include further curing the treatment fluid prior to removal of the surgical instrument and then fully curing the treatment fluid thereafter.

In some implementations of the method 1100, a control system may provide feedback to the surgeon to indicate that the treatment fluid has been partially cured to a desired point and that the surgeon may position the treatment fluid in contact with the tissue to be treated. For example, a timer may be triggered after a predetermined volume of treatment fluid is dispensed to the material applicator 105, or a timer may be triggered after a mixing operation occurs that combines reactive components of a self-curing treatment fluid. The timer may provide an audible or visual cue to the surgeon. Additionally, in implementations that include further curing the treatment fluid after contact with the tissue has been made, the control system may provide feedback, such as audio or video feedback, to indicate that the surgical instrument may be removed.

Implementations of the present disclosure may include surgical instruments that may be used, in ophthalmic and other intracavity procedures, to apply a treatment material to a treatment site, particularly where access to the treatment site is provided through a small incision. Additionally, methods of using such surgical instruments are described herein as well. Through use of the principles described herein, a surgeon can precisely shape and position a fluidic treatment material to facilitate adhesion of the treatment material to tissue or tissues at a desired treatment site. The treatment material may provide a structural barrier or structural support to surrounding tissue and may include one or more bioactive components that provide an additional therapeutic benefit to the tissue. The treatment material may also secure the tissue or tissues in a desired position to facilitate healing of the tissue or tissues. For example, implementations of the principles described herein may be utilized to seal a break in a retina or secure a torn retina in position for a period of weeks while the retina heals. Further, the treatment material may secure the torn retina in position without requiring the patient to maintain a specific head position.

Persons of ordinary skill in the art will appreciate that the implementations encompassed by the present disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of using a surgical instrument, the method comprising:
    inserting a distal end of the surgical instrument into a vitreous chamber of an eye;
    passing the distal end of the surgical instrument through the vitreous chamber and positioning the distal end of the surgical instrument at a retinal tissue;
    deploying a wicking member from the distal end of the surgical instrument;
    dispensing a volume of a treatment fluid from a lumen extending at least partially through the surgical instrument at the distal end of the surgical instrument, the volume of the treatment fluid being bound to the wicking member by microfluidic forces; and
    transferring the volume of the treatment fluid to the retinal tissue at a surgical treatment site.

2. The method of claim 1, further comprising partially curing the volume of the treatment fluid prior to transferring the volume of the treatment fluid to the retinal tissue at the surgical treatment site.

3. The method of claim 1, wherein the volume of the treatment fluid forms a treatment film.

4. The method of claim 1, wherein deploying the wicking member from the distal end of the surgical instrument and dispensing the volume of the treatment fluid from the lumen are performed simultaneously.

5. The method of claim 1,
    wherein the surgical instrument comprises an elongate tubular member having a proximal end, a distal end, and the lumen extending therebetween.

6. The method of claim 5, wherein deploying the wicking member comprises the wicking member extending beyond the distal end of the elongate tubular member, the wicking member configured to secure a volume of treatment fluid delivered through the lumen to the wicking member for application from the wicking member to the retinal tissue.

7. The method of claim 5, wherein the distal end of the elongate tubular member is capped and comprises a plurality of openings formed therein to permit the fluid to pass from the lumen to the fibers.

8. The method of claim 1, wherein the wicking member comprises a loop of material.

9. The method of claim 1, wherein the loop of material can be retracted into the lumen.

10. The method of claim 1, wherein the wicking member comprises a plurality of fibers.

11. The method of claim 10, wherein the fibers have a hydrophilic coating.

12. The method of claim 10, wherein the fibers are arranged in a generally circular configuration.

13. The method of claim 10, wherein the fibers are comprised of a polymer, glass, metal or shape-memory material.

14. The method of claim 10, wherein the fibers have an oval, square, rectangular, octagonal, or circular cross-section.

15. The method of claim 1, wherein the treatment fluid is a tissue adhesive.

16. The method of claim 1, wherein the wicking member has a rectangular cross-section.

17. The method of claim 1, wherein a diameter of the lumen is in approximately in a range of 0.2 mm (millimeters) to 0.6 mm.

* * * * *